United States Patent [19]

Davidson et al.

[11] 4,282,146

[45] Aug. 4, 1981

[54] PREPARATION OF 1,2,4,5-TETRAHYDRO-7-ALKOXY-(AND 7,8-DIALKOXY)-3H,3-BENZAZEPINES AND 3-SUBSTITUTED DERIVATIVES THEREOF FROM THE CORRESPONDING PHENETHYLAMINES

[75] Inventors: Thomas A. Davidson, Rochester; Ronald C. Griffith, Pittsford, both of N.Y.

[73] Assignee: Pennwalt Corporation, Philadelphia, Pa.

[21] Appl. No.: 962,223

[22] Filed: Nov. 20, 1978

[51] Int. Cl.$^3$ ........................................... C07D 223/16
[52] U.S. Cl. ............................... 260/239 BB; 564/374
[58] Field of Search .................................. 260/239 BB

[56] References Cited

U.S. PATENT DOCUMENTS 3,393,192  7/1968  Walter et al. .................. 260/239 BB
3,686,167  8/1972  Fujimura et al. ............... 260/239 BB

OTHER PUBLICATIONS

Olah Friedel–Crafts and Related Reactions, p. 223, vol. I, Interscience, NY (1963).
Likforman et al., Comptes Rendus, t268, 6/30/69, pp. 2340–2341.

Primary Examiner—Donald G. Daus
Assistant Examiner—D. B. Springer

[57] ABSTRACT

Certain 1,2,4,5-tetrahydro-7-alkoxy-(and 7,8-dialkoxy)-3H,3-benzazepines are prepared in excellent yields by a three step process comprising reacting a 3-alkoxy-(or 3,4-dialkoxy)-phenethylamine with a halo-acetaldehyde dialkylacetal to form the corresponding N-(2,2-dialkoxyethyl) phenethylamine, reacting that product with $BF_3$ to close the ring and to form a 1-alkoxy-1,2,3,4-tetrahydro-7-alkoxy-(or 7,8-dialkoxy)-3H,3-benzazepine and reacting that product under reductive cleavage conditions to remove the 1-alkoxy group and to obtain the desired benzazepine. The benzazepines can be further reacted in the known manner or in the manner disclosed herein to form certain 3-substituted benzazepines.

10 Claims, No Drawings

PREPARATION OF 1,2,4,5-TETRAHYDRO-7-ALKOXY-(AND 7,8-DIALKOXY)-3H,3-BENZAZEPINES AND 3-SUBSTITUTED DERIVATIVES THEREOF FROM THE CORRESPONDING PHENETHYLAMINES

BACKGROUND OF THE INVENTION

Many of the 1,2,4,5-tetrahydro-7-alkoxy-(and 7,8-dialkoxy)-3H,3-benzazepines which can be prepared by the process of this invention are known as a class. Their preparation and use as intermediates for conversion to various corresponding 3-substituted benzazepines is disclosed, for example, in U.S. Pat. No. 3,719,669 issued Mar. 6, 1973. The process of this invention constitutes an improved method for obtaining the benzazepine intermediates of U.S. Pat. No. 3,719,669 in fewer steps and in better yields.

DESCRIPTION OF THE PRIOR ART

A generalized disclosure of reaction steps analogous to those of this invention is disclosed by J. Likforman, and J. Gardent, in *Comptes Rendus Acad. Sc. Paris*, t 268, June 30, 1969, pp. 2340–41. The disclosed reaction is limited to the formation of benzazepines containing no ring substituents in the 7 or 8 positions and insufficient information is given as to conditions and proportions of reactants to enable performance of the process herein claimed.

BRIEF SUMMARY OF THE INVENTION

This invention relates to a process for the preparation of certain 1,2,4,5-tetrahydro-7-alkoxy-(and 7,8-dialkoxy)-3H,3-benzazepines in excellent yields by a three step process comprising:

(A) reacting a 3-alkoxy-(or 3,4-dialkoxy)-phenethylamine with a halo-acetaldehyde dialkylacetal to form the corresponding N-(2,2-dialkoxyethyl) phenethylamine;

(B) reacting the product of Step A with $BF_3$ to close the ring and to form a 1-alkoxy-1,2,4,5-tetrahydro-7-alkoxy-(or 7,8-dialkoxy)-3H,3-benzazepine; and (C) reacting the product of Step B under reductive cleavage conditions to remove the 1-alkoxy group and to obtain the desired benzazepine.

The benzazepines produced are valuable intermediates for a class of corresponding benzazepines which are substituted in the 3-position, such as the 3-substituted benzazepines disclosed in U.S. Pat. No. 3,719,669, the entire disclosure of which is incorporated herein by reference. The 3-substituted benzazepines disclosed in the patent (see Examples 10 and 11) are prepared, for example, by reacting the benzazepines of this invention which are unsubstituted in the 3-position with p-nitrophenylacetic acid to form a benzazepine substituted in the 3-position with a p-nitrophenylacetyl group followed by reduction of the nitro and amide moieties to produce the aminophenethyl group. In this manner or by analogous methods substituted benzazepines not disclosed in U.S. Pat. No. 3,719,669 can be prepared, namely, 3-(p-aminophenethyl)-1,2,4,5-tetrahydro-7,8-dimethoxy-3H,3-benzazepine hydrochloride and 3-(p-methylamino-phenethyl)-1,2,4,5-tetrahydro-7,8-dimethoxy-3H,3-benzazepine hydrochloride.

As disclosed in U.S. Pat. No. 3,719,669 the various 3-substituted benzazepines which can be prepared from the 3-unsubstituted benzazepines derived by the method of this invention are useful as analgesics and antagonists for narcotics such as morphine.

DETAILED DESCRIPTION OF THE INVENTION

The general reaction sequence of this invention is as follows.

(A) reacting

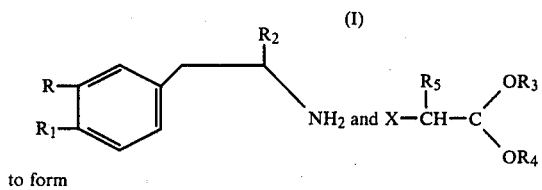

to form

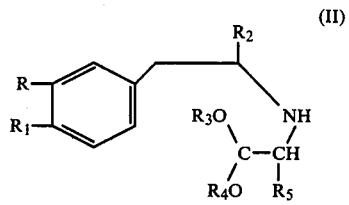

wherein
R is $C_1$–$C_4$-alkoxy;
$R_1$ is H or $C_1$–$C_4$-alkoxy; or
R and $R_1$ taken together are methylenedioxy;
$R_2$ is H or $C_1$–$C_4$-alkyl;
$R_3$ and $R_4$ are $C_1$–$C_4$-alkyl or taken together are ethylene;
$R_5$ is H, $C_1$–$C_4$-alkyl or phenyl;
X is halogen, preferably Cl or Br.

(B) reacting (II) with $BF_3$ to form

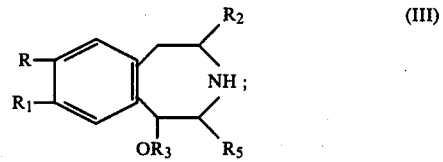

(C) subjecting (III) to reductive cleavage conditions to form

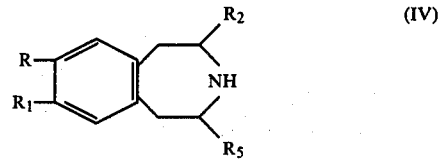

The phenethylamines used as starting materials in Step A and their methods of preparation are generally known in the literature. Certain of the phenethylamines can be advantageously prepared by the methods disclosed in abandoned application of Ronald C. Griffith, Ser. No. 948,874, filed Oct. 5, 1978, entitled "PROCESS FOR THE SYNTHESIS OF α-METHYL-PHENETHYLAMINES BY AMINOMERCURATION AND DEMERCURATION OR ALLYLBENZENES," the disclosure of which is incorporated herein by reference.

Step A is preferably conducted at elevated temperatures, e.g., 75° C. to 150° C. although higher or lower temperatures can be used. The reaction is preferably conducted in an inert organic solvent such as dimethyl formamide (DMF) and in the presence of a basic catalyst such as $K_2CO_3$.

It has been determined that Step B requires excess of $BF_3$, the amount of excess being dependent on the number of complexing sites present in the N-(2,2-dialkoxyethyl)-phenethylamine obtained from Step A. It is believed that this is because the $BF_3$ forms complexes with both the amino and alkoxy groups. Adjacent alkoxy groups may complex with one or two $BF_3$ molecules. Accordingly, where R and/or $R_1$ are alkoxy, a minimum of 3 moles of $BF_3$ per mole of the product of Step A are required for complexation and up to 2 moles additional $BF_3$ are advantageous to produce the product of Step B at a reasonable rate. Insufficient $BF_3$ results in a sluggish reaction or substantially no reaction. The $BF_3$ is preferably used in the form of its complex with diethylether or with ethanol, the ethanolate. The reaction B is conducted in an approximate solvent such as methylene chloride and at elevated temperatures, e.g., at reflux. The reaction does not proceed well at all at low temperatures as disclosed in the *Comptes Rendus* article referred to above.

Step C is advantageously and preferably conducted with sodium and anhydrous liquid ammonia as disclosed in the working Examples below or can be conducted by hydrogenation with a catalyst such as Pd.

The invention is illustrated by the non-limiting Examples which follow.

EXAMPLE 1

Preparation of
1,2,4,5-Tetrahydro-8-methoxy-3H,3-benzazepine

STEP A: Preparation of the
N-(2,2-Diethoxyethyl)-2-(3-methoxyphenyl)-1-methylethylamine

METHOD 1

2-(3-Methoxyphenyl)-1-methylethylamine (50 g, 0.303 M), potassium carbonate (100 g, 0.72 M) and dimethylformamide (250 ml) were mixed and heated to 110° C. Bromoacetaldehyde diethylacetal (65 g, 0.33 M) was added dropwise during 30 mins. The reaction was mildly exothermic. The temperature was maintained at 110°–130° C. for 1 hour. The cooled reaction mixture was filtered from the salts and the solvent was evaporated. The residual oil was distilled and the fraction boiling at 140°–143°/0.2 mm was collected. This is the desired aminoacetal, wt=59 g (70% yield).

METHOD 2

To a stirred solution of $Hg(NO_3)_2.H_2O$ (51.4 g, 0.15 mole) in tetrahydrofuran (100 ml) under $N_2$ was added aminoacetaldehyde diethylacetal (64 g, 69.9 ml, 0.48 mole) while cooling to maintain ambient temperature, and then m-allylanisole (17.8 g, 0.12 mole) was added and the mixture heated to 60° C. for 24 hours. After cooling to ambient, 10% NaOH (100 ml) and $NaBH_4$ (12.0 g, 0.32 mole) were added and the mixture stirred for 18 hours, acidified to pH 1 with 10% HCl, stirred until no more gas evolution was observed upon addition of small amounts of 10% HCl, then basified to pH 11 with 20% NaOH and extracted with $CHCl_3$ (3×500 ml), the extracts dried over $MgSO_4$ and evaporated to an oil, which was distilled under vacuum to remove the starting acetal and traces of m-allylanisole (b.p. 45°–68° C./0.05 mm). The pot residue was chromatographed (120 g $SiO_2$, 10% $MeOH/CHCl_3$) to give the product acetal as a yellow oil, 26.4 g (78% yield). (GC analyses, 86%).

STEP B: Preparation of
1-Ethoxy-1,2,4,5-tetrahydro-7-methoxy-4-methyl-3H,3-benzazepine

METHOD 1

To a stirred solution of $BF_3.O(CH_2CH_3)_2$ (100 g, 125 ml, 0.7 mole) in dry methylene chloride (2500 ml) maintained under nitrogen was added a solution of the N-(2,2-diethoxyethyl)-2-(3-methoxyphenyl)-1-methylethylamine (50 g, 0.178 mole) in dry methylene chloride (50 ml) and the mixture brought to reflux (40° C.) and stirred for 24 hours, cooled, and then quenched with $H_2O$ (125 ml), 5% NaOH (1500 ml) added to make the solution strongly basic, the layers separated and the aqueous phase extracted with methylene chloride (3×400 ml) and the combined organics dried over $MgSO_4$, filtered and the solvent evaporated to give a thick dark oil (64.5 g) which may be distilled directly or dissolved in warm benzene and passed through a bed of alumina to remove heavy and insoluble residues, then vacuum distilled to give a pale yellow oil (30.4 g, 73% yield) bp 120° C.–130° C./0.05 mm, corresponding to a ca 60%/40% mixture of the cis and trans epimeric ethers.

METHOD 2

A stirred mixture of anhydrous EtOH (64.4 g, 1.4 mole) in dry $CH_2Cl_2$ (1500 ml) maintained under $N_2$ was saturated with $BF_3$ gas (theory: 47.6 g, 0.7 mole) by passing the gas into the solution through a gas tube for 30 minutes. The mixture was stirred for 15 minutes and excess $BF_3$ gas removed by sweeping with nitrogen. To the solution which now contains $BF_3.(EtOH)_2$ (0.7 mole) was added the N-(2,2-diethoxyethyl)-2-(3-methoxyphenyl)-1-methylethylamine (50.0 g, 0.178 mole) in $CH_2Cl_2$ (50 ml) and the mixture heated at reflux for 4 hours, cooled to ambient, then poured into enough 10% NaOH (1200 ml) to obtain a pH of 11. The layers were separated and the aqueous phase extracted with $CH_2Cl_2$ (2×400 ml) and the combined extracts dried over $MgSO_4$ and evaporated to a thick orange-yellow oil. Distillation under vacuum gave the product as a thick pale yellow oil, 28.4 g (68% yield), bp 118°–132° C./0.05 mm.

STEP C: Preparation of
1,2,4,5-tetrahydro-8-methoxy-2-methyl-3H,3-benzazepine

METHOD 1

Anhydrous ammonia (200 ml) was condensed in a dry flask under nitrogen at −78° C. The flask was warmed to ca −33° C. and charged with absolute ethanol (6.37 g, 8.06 ml, 0.132 mole, 6.5 eq) and 1-ethoxy-1,2,4,5-tetrahydro-7-methoxy-4-methyl-3H,3-benzazepine (5.0 g, 0.0213 mole) making certain that all the ether had dissolved completely, and sodium pellets (1.0 g, 0.0435 mole, ~2 eq) were added successively over a period of 30 minutes. The ammonia was allowed to evaporate overnight to a pale yellow slurry to which water (100 ml), 5% NaOH (100 ml) and ethyl ether (200 ml) were added, the layers separated and the strongly basic aqueous phase extracted with ethyl ether (2×100 ml), the combined organic extracts dried over $MgSO_4$, filtered, and evaporated to give a pale yellow oil (3.9 g, 96% yield) which was shown by TLC and IR to consist of >95% benzazepine. Vacuum distillation gave a colorless oil (3.2 g) bp 88°-90° C. /0.05 mm; pure benzazepine.

METHOD 2

A solution of the 1-ethoxy-1,2,4,5-tetrahydro-7-methoxy-4-methyl-3H,3-benzazepine (10 g, 0.0426 mole) in acetic acid (100 ml) and concentrated HCl (5 ml) with 5% Pd/C (1 g) catalyst was hydrogenated at 50 psi and 30° C. for 72 hours. The catalyst was removed by filtration, and the solvent evaporated to an oil which was basified with 10% NaOH (200 ml) and extracted with ethyl ether (3×150 ml), the extracts dried over MgSO4 and evaporated to give 6.6 g (89% yield) of an oil (90% conversion to the product benzazepine). Vacuum distillation (bp 94°-95° C./0.05 mm) afforded the pure product as a pale yellow oil.

EXAMPLE 2

Preparation of 3-(4-methylaminophenethyl)-1,2,4,5-tetrahydro-7,8-dimethoxy-3H,2-benzazepine STEP A: Preparation of N-(2,2-diethoxyethyl)-3,4-dimethoxy-phenethylamine To a stirred suspension of anhydrous potassium carbonate (300 g) and 3,4-dimethoxyphenethylamine (148 g, 0.818 m) in dimethylformamide (750 ml) under $N_2$ at 110° C. was added dropwise over 30 min bromoacetaldehyde diethylacetal (167.5 g, 0.850 m). During the addition, the temperature was allowed to rise to 130° C., maintained at 125°-130° C. for 1.5 hrs, then cooled. At ca 40° C., 70 ml of water was added, stirred for 1 hr, then the salts removed by filtration and the solvent evaporated to a volume of ca 300 ml. Ether (750 ml) was added, the precipitated solid was filtered and the filtrate evaporated to an oil, 247 g. This material was vacuum-distilled to give three fractions: (1) b.p. 30°-154° C./0.1 mm, 17.0 g; (2) b.p. 154°-157° C./0.1 mm, 171.6 g; (3) b.p. 157°-174° C./0.1 mm, 37.3 g. Fraction (2) contained the product in 71% yield.

STEP B: Preparation of 1-Ethoxy-1,2,4,5--tetrahydro-7,8-dimethoxy-3H,3-benzazepine To a stirred solution of boron trifluoride etherate (83.66 g, 72.5 ml, 9.589 m) in methylene chloride (2500 ml) at ambient temperature under $N_2$ was added dropwise a solution of the N-(2,2-diethoxyethyl)-3,4-dimethoxyphenethylamine (50.0 g, 0.168 m) in methylene chloride (100 ml). The mixture was stirred for 2 hrs, then heated to a gentle reflux (40° C.) for 16 hrs. The mixture was cooled with an ice bath to 10°-15° C. and 5% NaOH (1200 ml) added rapidly and stirred vigorously for 15 min, then poured into a separatory funnel, the organic phase removed and the aqueous phase extracted with 2×200 ml methylene chloride, and the combined organic layers dried over sodium sulfate. Removal of the drying agent by filtration and evaporation of the solvent gave an oil, 51.0 g. This material was chromatographed on silica gel (100 g), eluting with 10% methanol/chloroform. The fractions containing pure product were combined and evaporated to give a yellow oil, 29.5 g (70% yield).

STEP C: Preparation of 1,2,4,5-tetrahydro-7,8-dimethoxy-3H,3-benzazepine

To a stirred solution of 1-ethoxy-1,2,4,5-tetrahydro-7,8-dimethoxy-3H,3-benzazepine (42.9 g, 0.17 m) and absolute ethanol (51.06 g, 64.63 ml, 1.11 mole, 6.5 M excess) in anhydrous ammonia (1500 ml) maintained at the reflux temperature under nitrogen, where added small pieces of sodium (7.81 g, 0.34 m) one at a time, waiting until the previous piece had dissolved before addition of another. After the addition was complete, the ammonia was allowed to evaporate under a stream of nitrogen, leaving a white solid. Water (1000 ml) was added, stirred 5 min, then $CHCl_3$ (500 ml) added, stirred 5 min, layers separated and the aqueous phase extracted with 2×200 ml $CHCl_3$ and the combined organic layers dried over magnesium sulfate, filtered and evaporated to a pale yellow solid, 34.1 g (96% yield). This material was dissolved in hot cyclohexane (200 ml), treated with activated charcoal, hot filtered and allowed to crystallize. Filtration of the formed crystals gave the product as a pale yellow solid, 28.4 g (81% yield), m.p. 93.5°-94.0° C.

STEP D: Preparation of 1,2,4,5-Tetrahydro-7,8-dimethoxy-3-(4-nitrophenylacetyl)-3H,3-benzazepine To a stirred solution of 1,2,4,5-tetrahydro-7,8-dimethoxy-3H,3-benzazepine (11.6 g, 0.056 m) in THF (40 ml) under $N_2$ at RT, was added a solution of dicyclohexylcarbodiimide (DCC) (12.7 g, 0.0616 m) in THF (40 ml) and then a solution of p-nitrophenylacetic acid (11.3 g, 0.062 m) in THF (50 ml). The mixture was stirred for 2 hrs, acetic acid (0.5 ml) was added and stirred for 15 min to convert all unreacted DCC, and the precipitated dicyclohexylurea removed by filtration. The solid thus obtained was slurried with hot THF, filtered and the combined filtrates evaporated to afford the light yellow solid product, 21.7 g, contaminated with a small amount of dicyclohexylurea. (100+% yield).

STEP E: Preparation of 3-(4-Aminophenylacetyl)-1,2,4,5-tetrahydro-7,8-dimethoxy-3H,3-benzazepine A solution of 1,2,4,5-tetrahydro-7,8-dimethoxy-3-(4-nitrophenylacetyl)-3H,3-benzazepine (21.7 g, theory 20.7 g, 0.056 m) in 1000 ml 1:1 methanol:ethylacetate and 8 ml conc HCl/10 ml $H_2O$ was hydrogenated on a Parr shaker over 2.0 g 10% Pd/C at ambient temperature and 50 psi. After 1.5 hrs, uptake of hydrogen was complete. The catalyst was removed by filtration and washed with hot ethyl acetate. (Caution: Some product may crystallize out and be removed with the catalyst.) The solvent was evaporated, and the residue dissolved in 1000 ml $H_2O$ and filtered to remove dicyclohexylurea carried from the previous reaction. The filtrate was basified to pH 11 with 10% NaOH, extracted with 3×300 ml $CHCl_3$ and the extracts dried over $MgSO_4$, and evaporated to afford the product as a white solid, 16.6 g (88% yield).

STEP F: Preparation of 3-(4-aminophenethyl)-1,2,4,5-tetrahydro-7,8-dimethoxy-3H,3-benzazepine

METHOD 1

To a stirred suspension of lithium aluminum hydride (7.42 g, 0.1952 m, 4 molar excess) in 200 ml dry THF under $N_2$ at ambient temperature was added dropwise a solution of 3-(4-aminophenylacetyl)-1,2,4,5-tetrahydro-7,8-dimethoxy-3H,3-benzazepine (16.6 g, 0.0488 m) in 200 ml dry THF which was heated to obtain a solution.

The mixture was stirred for 2 hrs at ambient temperature, then cooled with an ice bath and quenched with 10% NaOH (16 ml), stirred for 1 hr, then the precipitated salts removed by filtration and the solvent evaporated to afford the crude product as an off-white solid, 14.2 g (89%). This material was purified by chromatography on alumina saturated with ammonia, eluting with 10% ether/CHCl$_3$ and afforded 11.9 g (75%) pure product.

Alternatively, the free base may be purified by crystallization from cyclohexane, or better, from 95% ethanol, the latter of which gives a white solid, m.p. 156.5°–157° C.

The bis-hydrochloride salt is prepared by acidifying a 2/1 MeOH/THF solution of the free base with HCl gas, followed by charcoal treatment and crystallization and may be recrystallized from absolute ethanol or 95% ethanol and ether. The solid product obtained melts at 233°–235° C. dec. and is hydrated with water.

METHOD 2

To a stirred solution of 0.94 M borane in THF (158.8 ml, 0.149 m) under N$_2$ at room temperature was added as a solid, 3-(4-aminophenylacetyl)-1,2,4,5-tetrahydro-7,8-dimethoxy-3H,3-benzazepine (24.2 g, 0.071 m). The mixture was stirred for 1 hr, then heated to reflux for 1 hr, and cooled to ambient overnight. THF (100 ml) was added and the mixture cooled with an ice water bath and treated with 10% HCl (100 ml). The mixture was transferred to a rotary evaporator and the THF slowly removed at 50° C. (water aspirator). After ca 100 ml THF was collected, an additional 100 ml 10% HCl was added and all remaining THF removed. The aqueous residue was diluted with 200 ml H$_2$O and extracted with 3×250 ml CHCl$_3$. The aqueous phase was basified to pH 11 with NaOH and extracted with 3×300 ml CHCl$_3$, the extracts dried over MgSO$_4$ and evaporated to a pale yellow solid, 22.3 g (96% yield). The solid was recrystallized from 95% Ethanol (150 ml) to give 18.2 g product. (79% yield).

STEP G: Preparation of 3-(4-Formamidophenethyl)-1,2,4,5-tetrahydro-7,8-dimethoxy-3H,3-benzazepine To a stirred solution/suspension of 3-(4-aminophenethyl)-1,2,4,5-tetrahydro-7,8-dimethoxy-3H,3-benzazepine (5.6 g, 0.01718 m) in toluene (50 ml) was added 10 ml 97% formic acid and the mixture heated to reflux, collecting the toluene insoluble material in a Dean-Stark tube. After 7 ml had been collected (ca 1.5 hr), the mixture was cooled, dissolved in water (250 ml), basified to pH 11 with 15% NaOH and extracted with chloroform (3×100 ml). The extracts were dried over MgSO$_4$ and evaporated to afford the product as an off-white solid, 7.5 g (100+% yield due to entrapped toluene). This material showed a single spot on TLC and was used as in the next reaction.

STEP H: Preparation of 3-(4-methylaminophenethyl)-1,2,4,5-tetrahydro-7,8-dimethoxy-3H,3-benzazepine To a stirred suspension of lithium aluminum hydride (3.2 g, 0.0848 m) in dry THF (100 ml) under N$_2$ at ambient temperature was added dropwise a solution of the formamide (7.5 g, theory 6.1 g, 0.01718 m) in 50 ml dry THF and the mixture stirred for 2.0 hrs, cooled with an ice bath and quenched with a solution of 15 ml H$_2$O, 1 ml 15% NaOH, and 5 ml THF. The mixture was stirred 30 min, salts removed by filtration and the filtrate evaporated to dryness to give the product as a white solid, 5.1 g (87% yield). TLC showed a single spot. Recrystallization from 95% ethanol gave 3.2 g of a white solid, m.p. 129.5°–130.5° C. and a second crop of 1.5 g.

EXAMPLE 3

Preparation of 3-(4-Aminophenethyl)-1,2,4,5-tetrahydro-7,8-dimethoxy-3H,3-benzazepine dihydrochloride STEP A: Preparation of N-(2,2-diethoxyethyl)-3,4-dimethoxyphenethylamine To a stirred suspension of anhydrous potassium carbonate (300 g) and 3,4-dimethoxyphenethylamine (148 g, 0.818 m) in dimethylformamide (750 ml) under N$_2$ at 110° C. was added dropwise over 30 min bromoacetaldehyde diethylacetal (167.5 g, 0.850 m). During the addition, the temperature was allowed to rise to 130° C., maintained at 125°–130° C. for 1.5 hours, then the solution cooled. At ca 40° C., 70 ml of water were added, the mixture was stirred for 1 hour, then the inorganic salts were removed by filtration and the solvent evaporated. n-Hexane (750 ml) was added, the precipitated solid was filtered and the filtrate evaporated to an oil, 247 g. This material was vacuum-distilled to give three fractions: (1) b.p. 30°–154° C./0.1 mm, 17.0 g; (2) b.p. 154°–157° C./0.1 mm, 171.6 g; (3) b.p. 157°–174° C./0.1 mm, 37.3 g. Fraction (2) contained the product in 71% yield and 86% purity (GLC).

STEP B: Preparation of 1-Ethoxy-1,2,4,5-tetrahydro-7,8-dimethoxy-3H,3-benzazepine To a reaction flask, flushed out with N$_2$, was added CH$_2$Cl$_2$ (1.617 liters) and pure abs ethanol (52.9 g, 1.148 mol). The solution was cooled in an ice-H$_2$O bath, and, while stirring, BF$_3$ gas (77.9 g, 1.148 mol) was introduced into the solution at such a rate that complete absorption took place, and the temperature was maintained at 5°–10° C.

To the above solution was added N-(2,2-diethoxyethyl)-3,4-dimethoxy-phenethylamine [85.44 g (85–90% pure, 0.287 mol] dissolved in CH$_2$Cl$_2$ (85 ml) over a one-half hour period while maintaining the temperature at approximately 5°–7° C. The mixture was then refluxed for 17 hours. A tlc check was made for completion of reaction before work-up. If the reaction was not complete, the reflux time was extended. The reaction mixture was then cooled, using an ice-water bath, and the temperature maintained at 20°–30° C. while 1.128 liters of 2.5 N NaOH (or sufficient to obtain a pH of 10 to 11) was added with stirring. After stirring one-half hour, the pH was checked and 2.5 N NaOH added, if necessary. The organic layer was separated and the aqueous layer washed with 2×60 ml portions of CH$_2$Cl$_2$. The combined CH$_2$Cl$_2$ layers were washed with 4×300 ml portions of water and then dried over MgSO$_4$. Removal of the solvent yielded 75.6 g (105%) of the crude product as a thick dark oil. This analyzed as approximately 76% product (GLC).

STEP C: Preparation of 1,2,4,5-Tetrahydro-7,8-dimethoxy-3H,3-benzazepine

Anhydrous ammonia (2 liters) was condensed into a dry N$_2$-flushed flask. A solution of 1-ethoxy-1,2,4,5-tetrahydro-7,8-dimethoxy-3H,3-benzazepine [95.6 g (approximately 76% pure), 0.38 mol] in absolute ethanol (144 ml) was added dropwise, with stirring to the liquid ammonia at approximately −33° C. Sodium pellets (17.4 g, 0.76 mol) were added to the above solution over a period of one to two hours. Upon completion of the addition, the dry-ice condenser was removed and the ammonia allowed to evaporate, leaving a pale yellow solid. Water (300 ml) was added and the product extracted into chloroform (3×100 ml). The combined extracts were washed with water (4×50 ml) and then dried over MgSO$_4$. Removal of the chloroform in a rotovap yielded 82.0 g (104%) of crude product as a thick oil that solidified readily. This analyzed as approximately 67% product (GLC).

The above crude was purified by isolation of the product as the carbonate salt. The crude product was dissolved in 418 ml of acetone with the aid of some heat. Dry ice was then added to the solution, and a solid formed immediately. The mixture was allowed to warm to room temperature, and the product was then filtered and washed with acetone (approximately 100 ml, or until wash was colorless), yield 50 g., mp 125°-150° C. (dec).

STEP D: Preparation of 1,2,4,5-Tetrahydro-7,8-dimethoxy-3-(4-nitrophenylacetyl)-3H,3-benzazepine To a stirred suspension of 1,2,4,5-tetrahydro-7,8-dimethoxy-3H,3-benzazepine carbonate (45.3 g) in 362 ml CH$_2$Cl$_2$, under nitrogen, was added 39.6 g of p-nitrophenylacetic acid. A solution was obtained with the evolution of CO$_2$. To the above solution was added dropwise 45.1 g dicyclohexylcarbodiimide (DCC) dissolved in 165 ml CH$_2$Cl$_2$ while maintaining the temperature at 20° C. A tlc check showed the reaction to be complete after one hour. Glacial acetic acid (2.0 ml) was added and the mixture stirred for one-half hour. The precipitated dicyclohexylurea (DCU) was removed by filtration and the DCU washed with 180 ml CH$_2$Cl$_2$ until it was free of color. The filtrate was concentrated to a slurry on a rotovap to yield a semi-solid residue. This was treated with 200 ml of refluxing methanol for a few minutes to drive off any CH$_2$Cl$_2$ and the mixture then allowed to cool. The product was filtered and washed with 100 ml of methanol, yield 66.6 g of product as a bright yellow solid, mp 155°-157° C.

STEP E: Preparation of 1,2,4,5-Tetrahydro-7,8,dimethoxy-3-(4-nitrophenethyl)-3H,3-benzazepine hydrochloride To 104.7 g (0.283 mol) of 1,2,4,5-tetrahydro-7,8-dimethoxy-3-(4-nitrophenylacetyl)-3H,3-benzazepine in 960 ml of THF was added 72.3 ml (0.723 mol) of borane-methyl sulfide complex (BMS). The reaction mixture was refluxed for 1.5 to 2 hours and checked for completion of reaction by tlc. The mixture was then cooled and 165 ml of methanol was added dropwise while maintaining the temperature at 20°-25° C. There was considerable foaming during the addition of the first 50 ml of methanol. This was followed by the addition of 329 ml of 2.5 N HCl. The clear yellow solution was then refluxed for one hour. A tlc check showed the boron-amine complex essentially gone. The THF and methanol were then rapidly distilled off. When the pot temperature reached 84° C. and the head temperature 75° C., the distillation of the solvents was essentially complete. The volume remaining was approximately 400 ml. To this was added 165 ml of methanol and 165 ml of water and the mixture reheated to effect solution. The solution was then allowed to cool to room temperature, with stirring, until crystallization was complete. The product was filtered, washed with 200 ml 25% methanol and air dried; yield 103.0 g of the hydrochloride, m.p. 110°-120° C.

STEP F: Preparation of 3-(4-Aminophenethyl)-1,2,4,5-tetrahydro-7,8-dimethoxy-3H,3-benzazepine A mixture of 92.7 g of 1,2,4,5-tetrahydro-7,8-dimethoxy-3-(4-nitrophenethyl)-3H,3-benzazepine hydrochloride, 1000 ml water, 165 ml 2.5 N HCl and 7.0 g 5% Pd/C was treated with hydrogen at 50 psi in a Parr Hydrogenator. After the theoretical amount of hydrogen was taken up over approximately 1 to 2 hours, the catalyst was filtered off. The clear colorless filtrate was then treated with 2.5 N NaOH. Just before the solution turned cloudy, the mixture was seeded or crystallization initiated. Once crystallization was well-established, the 2.5 N NaOH addition was continued until a pH of 9 was obtained. A total of 220 ml of 2.5 N NaOH was required. After stirring 1 hour at room temperature, the product was filtered and washed with 350 ml water. After air drying, the product weighed 62.8 g, m.p. 161°-163.5° C.

STEP G: Preparation of 3-(4-Aminophenethyl)-1,2,4,5-tetrahydro-7,8-dimethoxy-3H,3-benzazepine dihydrochloride Dry HCl was introduced into a mixture of 62.1 g of 3-(4-aminophenethyl)-1,3,4,5-tetrahydro-7,8-dimethoxy-3H,3-benzazepine and 500 ml of methanol until the mixture tested strongly acid. The heat of reaction solubilized the salt formed. Additional heat was applied when necessary to obtain a solution To the hot solution was added 500 ml of isopropanol and the mixture allowed to cool to room temperature with occasional stirring. The mixture was then cooled at 15° C. for 0.5 hour, filtered and the product washed with 250 ml isopropanol, yield 78 g of dried product. This was recrystallized by dissolving it in 600 ml of hot methanol, treating the hot solution with 10 g decolorizing charcoal and then adding 600 ml isopropanol to the hot colorless filtrate. After cooling in the manner described above, the product was filtered and washed with 200 ml isopropanol. The damp cake was dried in a fluid bed dryer for 0.75 hour, yield 62.9 g, mp.o. 235°-237° C. (dec). The product is off-white in color and should be stored under nitrogen, protected from light.

EXAMPLE 4

Preparation of (−)-1,2,4,5-Tetrahydro-8-methoxy-2-methyl-3H,3-benzazepine

STEP A: Preparation of (+)-N-(2,2-Diethoxyethyl)-2-(3-methoxyphenyl)-1-methylethylamine (+)-2-(3-methoxyphenyl)-1-methylethylamine (472.8 g, 2.86 mol), potassium carbonate (sesquihydrate) (1133.8 g, 6.88 mol) and dimethylformamide (2400 ml) were mixed and heated to 130° C. in a reaction flask fitted with an efficient stirrer and a reflux condenser. Bromoacetaldehyde diethylacetal (630 g, 3.20 mol) was added dropwise over a 45 min period while maintaining the temperature at 130° C. The reaction was mildly exothermic. The temperature was maintained at 130° C. for 1 hr. The reaction mixture was cooled to 45° C., and 325 ml of water was added. After stirring at least 1 hr and after the temperature of the mixture reached 30°, it was filtered from the salts and the solvent evaporated under vacuum on a rotatory evaporator. The residual oil was filtered from some inorganic salts and distilled under vacuum; collected fractions boiling at 115°–130° C. at 0.05 mmHg, yield 68% of (+)-N-(2,2-diethoxyethyl)-2-(3-methoxyphenyl)-1-methylethylamine.

STEP B: Preparation of (−)-1-Ethoxy-1,2,4,5-tetrahydro-7-methoxy-4-methyl-3H,3-benzazepine To a reaction flask, flushed out with $N_2$, was added $CH_2Cl_2$ (3 liters) and pure abs ethanol (129.3 ml, 2.24 mol). The solution was cooled in an ice-$H_2O$ bath, and, while stirring, $BF_3$ gas (151.9 g, 2.24 mol) was introduced into the solution at such a rate that complete absorption took place, and the temperature was maintained at 5°–10° C. The took approximately one hour.

To the above solution was added (+)-N-(2,2diethoxyethyl)-2-(3-methoxyphenyl)-1-methylethylamine (150.0 g, 0,533 mol) dissolved in $CH_2Cl_2$ (150 ml) over a ½-hour period while maintaining the temperature at approximately 5° C. The mixture was then refluxed for 19 hours. A tlc check was made for completion of reaction before work-up. If the reaction was not complete, the reflux time was extended. The reaction mixture was then cooled, using a cold water bath, and 2.1 liters of 2.5 N NaOH (or sufficient to obtain a pH of 10 to 11) was added with stirring. The temperature rose to 34° C. from the slightly exothermic reaction. After stirring ½ hour, the pH was checked and 2.5 N NaOH added, if necessary. The organic layer was separated and the aqueous layer washed with 2×100 ml portions of $CH_2Cl_2$. The combined $CH_2Cl_2$ layers were washed with 2×200 ml portions of water and then dried over $MgSO_4$. Removal of the solvent yielded 126 g of the crude product. This was distilled under vacuum to give 93.5 g (74.6%) of the product boiling at 100°–125° C. at 0.1 to 0.3 mmHg as a mixture of the cis and trans epimeric ethers (60/40).

STEP C: Preparation of (−)-1,2,4,5-Tetrahydro-8-methoxy-2-methyl-3H,3-benzazepine Anhydrous ammonia (8.8 liters) was condensed into a dry, $N_2$ flushed flask. A solution of (−)-1-ethoxy-1,2,4,5-tetrahydro-7-methoxy-4-methyl-3H,3-benzazepine (405.5 g, 1.72 mol) in absolute ethanol (669 ml, 11.6 mol) was added dropwise, with stirring, to the liquid ammonia at approximately −33° C. (1). Sodium pellets (87.3 g, 3.80 mol) were added to the above solution over a period of one to two hours. Upon completion of the addition, the dry-ice condenser was removed and the ammonia allowed to evaporate, leaving a pale yellow solid. Water (3.3 liters) was added and the product extracted into $CHCl_3$ (1×1465 ml, 2. 700 ml). The combined extracts were washed with water and then dried over $MgSO_4$. Removal of the $CHCl_3$ on a rotovap yielded 403 g of crude product. This was distilled under vacuum and the fraction boiling at 78°–81° C. at 0.01 mmHg collected to give (−)-1,2,4,5-tetrahydro-8-methoxy-2-methyl-3H,3-benzazepine (263 g, 80%).

We claim:

1. In a process for preparing 1-alkoxy-1,2,4,5-tetrahydro-3H,3-benzazepines by ring closure of N-(2,2-dialkoxyethyl)phenethylamines with $BF_3$, the improvement which comprises the step of reacting a N-(2,2-dialkoxyethyl)phenethylamine having the formula

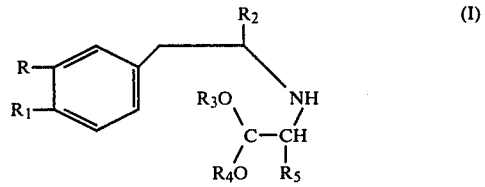

(I)

with an excess of $BF_3$ complex selected from $BF_3$ etherate or $BF_3$ ethanolate, in an inert solvent at elevated temperatures, to form

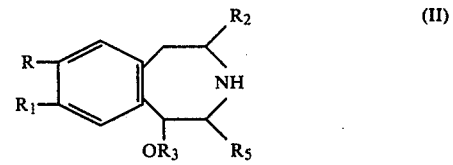

(II)

wherein:
R is $C_1$–$C_4$ alkoxy;
$R_1$ is H or $C_1$–$C_4$ alkoxy; or
R and $R_1$ taken together are methylenedioxy;
$R_2$ is H or $C_1$–$C_4$ alkyl;
$R_3$ and $R_4$ are $C_1$–$C_4$ alkyl; and
$R_5$ is H, $C_1$–$C_4$ alkyl or phenyl.

2. The process of claim 1 which further comprises the step of subjecting compound II to reductive cleavage conditions to replace the 1-alkoxy group with hydrogen.

3. The process of claim 2 in which $R_2$ is $C_1$–$C_4$ alkyl, $R_5$ is hydrogen and compounds I and II are the optical isomers asymmetric at the $R_2$ attachment.

4. The process of claim 2 in which the reductive cleavage step is conducted in the presence of sodium and anhydrous liquid ammonia.

5. The process of claim 2 in which the $BF_3$ complex is $BF_3$ ethanolate.

6. The process of claim 2 in which $R_2$ is H.

7. The process of claim 2 in which $R_2$ is $CH_3$.

8. The process of claim 2 in which $R_5$ is H.

9. The process of claim 2 in which R and $R_1$ are methoxy and $R_2$ is H.

10. The process of claim 2 in which
R is methoxy,
$R_1$ is H, and
$R_2$ is $CH_3$.

* * * * *